(12) United States Patent
Denti et al.

(10) Patent No.: US 7,753,898 B2
(45) Date of Patent: *Jul. 13, 2010

(54) TAMPON HAVING INDICATOR ENCLOSED IN A TAMPON APPLICATOR

(75) Inventors: Federica Denti, Schwalbach am Taunus (DE); Beate Rosemarie Stellbrink, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 411 days.

This patent is subject to a terminal disclaimer.

(21) Appl. No.: 11/196,626

(22) Filed: Aug. 3, 2005

(65) Prior Publication Data

US 2006/0167430 A1 Jul. 27, 2006

Related U.S. Application Data

(63) Continuation of application No. 11/040,154, filed on Jan. 21, 2005, now Pat. No. 7,175,616.

(51) Int. Cl.
*A61F 13/15* (2006.01)
*A61F 13/20* (2006.01)

(52) U.S. Cl. .............. 604/385.18; 604/385.17; 604/904

(58) Field of Classification Search .......... 604/11–15, 604/385.17, 904, 385.18; 424/430, 431
See application file for complete search history.

(56) References Cited

U.S. PATENT DOCUMENTS

| | | | |
|---|---|---|---|
| 2,123,750 | A | 7/1938 | Schulz |
| 3,738,364 | A | 6/1973 | Brien et al. |
| 3,854,481 | A | 12/1974 | Messing |
| 3,946,737 | A | 3/1976 | Kobler |
| 4,326,527 | A | 4/1982 | Wollangk et al. |
| 4,591,523 | A | 5/1986 | Thompson |
| 4,609,518 | A | 9/1986 | Curro et al. |
| 4,629,643 | A | 12/1986 | Curro et al. |
| 4,685,178 | A | 8/1987 | Nakanishi |

(Continued)

FOREIGN PATENT DOCUMENTS

EP    0 422 660 B1    2/1994

(Continued)

OTHER PUBLICATIONS

PCT International Search Report dated Jul. 28, 2006.

*Primary Examiner*—Melanie J Hand
(74) *Attorney, Agent, or Firm*—James E. Oehlenschlager

(57) ABSTRACT

An array of disposable absorbent articles. The array has a first absorbent article and a second absorbent article. The first absorbent article is enclosed in a first tampon applicator having i.) an outer surface wherein the outer surface has an outer surface area and ii.) a first identifier having a first surface area. The first identifier is disposed on the first absorbent article and corresponds to a first absorbency. The first identifier is disposed on the first absorbent article. A second absorbent article is enclosed in a second tampon applicator having i.) an outer surface wherein the outer surface has an outer surface area and ii.) a second identifier having a second surface area. The second identifier is disposed on the second absorbent article and corresponds to a second absorbency. The first surface area is different than the second surface area.

18 Claims, 12 Drawing Sheets

U.S. PATENT DOCUMENTS

| | | | |
|---|---|---|---|
| 4,839,216 A | 6/1989 | Curro et al. | |
| 4,951,368 A | 8/1990 | Heinen | |
| 5,087,239 A * | 2/1992 | Beastall et al. | 604/14 |
| 5,153,971 A | 10/1992 | Van Iten | |
| 5,279,541 A * | 1/1994 | Frayman et al. | 604/14 |
| 5,350,371 A | 9/1994 | Van Iten | |
| 5,531,325 A * | 7/1996 | Deflander et al. | 206/494 |
| 5,592,725 A | 1/1997 | Brinker | |
| 5,738,646 A | 4/1998 | Fox et al. | |
| 5,788,910 A | 8/1998 | McNeilis et al. | |
| 5,832,576 A | 11/1998 | Leutwyler et al. | |
| 5,891,081 A | 4/1999 | McNelis et al. | |
| 5,911,712 A | 6/1999 | Leutwyler et al. | |
| 5,958,321 A | 9/1999 | Schoelling et al. | |
| 6,003,216 A | 12/1999 | Hull, Jr. et al. | |
| 6,071,259 A | 6/2000 | Steiger et al. | |
| 6,093,027 A | 7/2000 | Unger et al. | |
| 6,156,021 A | 12/2000 | Tojkander | |
| 6,283,952 B1 | 9/2001 | Child et al. | |
| 6,310,269 B1 | 10/2001 | Friese et al. | |
| 6,601,705 B2 * | 8/2003 | Molina et al. | 206/494 |
| 6,679,705 B2 * | 1/2004 | Supinski et al. | 434/429 |
| 7,144,391 B1 * | 12/2006 | Kreutz et al. | 604/385.17 |
| 2002/0016579 A1 | 2/2002 | Stenberg | |
| 2002/0151859 A1 | 10/2002 | Schoelling | |
| 2003/0078553 A1 | 4/2003 | Wada et al. | |
| 2003/0120241 A1 * | 6/2003 | Sorebo et al. | 604/385.02 |
| 2003/0176845 A1 * | 9/2003 | Kollwitz et al. | 604/385.17 |
| 2003/0236485 A1 * | 12/2003 | Fedyk et al. | 604/11 |
| 2004/0050738 A1 | 3/2004 | Molina et al. | |
| 2004/0102748 A1 | 5/2004 | Hirotsu | |
| 2005/0209576 A1 * | 9/2005 | Hirotsu | 604/385.02 |
| 2006/0069372 A1 | 3/2006 | Chakravarty et al. | |
| 2006/0111662 A1 * | 5/2006 | Karapasha et al. | 604/16 |
| 2006/0129114 A1 | 6/2006 | Mason, Jr. et al. | |
| 2006/0129116 A1 | 6/2006 | Hughes et al. | |
| 2006/0135927 A1 | 6/2006 | Zander et al. | |

FOREIGN PATENT DOCUMENTS

| | | |
|---|---|---|
| EP | 1 666 012 | 6/2006 |
| WO | WO 00/37013 A1 | 6/2000 |
| WO | WO 01/66055 A1 | 9/2001 |
| WO | WO 02/078586 A3 | 10/2002 |

* cited by examiner

TAMPON HAVING INDICATOR ENCLOSED IN A TAMPON APPLICATOR

CROSS REFERENCE TO RELATED APPLICATION

This application is a continuation of U.S. application Ser. No. 11/040,154 filed Jan. 21, 2005, now U.S. Pat. No. 7,175,616.

FIELD OF THE INVENTION

This invention relates to tampons, and more particularly to tampons comprising an indicator enclosed in a tampon applicator.

BACKGROUND OF THE INVENTION

Surprisingly, some of the problems associated with the proper selection and use of such products are traceable to modern developments in the technologies used to improve their performance. In the past, the absorbency of catamenials, as well as other absorbent articles such as tampons, baby diapers, and adult incontinence garments, could be estimated by visual inspection of their size, shape, and bulk. However, improvements made in modern absorbent articles in an effort to increase in-use comfort and to increase the compactness for ease-of-packaging have resulted in the development of thin, and even ultra-thin, products. Rather than relying on size and bulk to achieve absorbency, such modern articles typically employ absorbent gelling materials (hereinafter "AGM"; "superabsorbents"), new methods of forming absorbent batts or pads of cellulosic fibers, and/or various structural improvements to achieve the desired absorbency. Whatever the technology, the result is that the performance or absorbent capacity of such articles can no longer be reliably judged solely on the basis of their size and bulk.

In addition to improvements in technology, improvements made in modern absorbent articles in an effort to increase in-use comfort and consumer satisfaction have resulted in the proliferation of sizes, shapes, conformations and brands in the field of disposable absorbent articles such as feminine care articles. Because of the proliferation of sizes, shapes, conformations and brands in the field of disposable absorbent articles, customers have difficulty differentiating between the many types of articles and the variations of article characterizations within these article types. In other words, differentiation and selection of absorbent articles is difficult due to the many types of articles and variations of article characterizations within these article types. For example, differentiation and selection of catamenial articles are particularly difficult due to the many choices of article absorbencies such as: light absorbency, regular absorbency, and extra absorbency and article configurations, for example, daytime articles, nighttime articles, winged versions and the like. Differentiation and selection of articles is also particularly difficult when there is not any artwork, color, and/or shape which differentiates each type of absorbent article.

Often color is used to convey a particular performance characteristic of a given article. For example, at least one manufacturer of catamenial tampon applicator uses color-based signals on both the outer packaging and the wrapper of such tampon applicators to denote absorbent capacity. In such articles, different colors are used to represent different article characteristic levels (in this case absorbency). For example, a green band on the package and wrapper of a tampon applicator might signal a "super" absorbency tampon, while a blue band might signal a "regular" absorbency tampon.

However, it is problematic when the tampon applicator is removed from the wrapper and/or package and there is not any indication of the type of product absorbency. Thus, there is a need for an intuitive method of signaling to the user the absorbency which is independent of the packaging and/or wrapper when the tampon applicator is then removed from the original container and placed in the bathroom drawer, purse, etc.

Proper selection of consumer articles requires an explicit signal. Despite considerable attention being given to such matters, mistakes continue to be made by consumers. In some instances, the consumer may be inattentative to the packaging which signals the absorbency or unable to determine the thinness or thickness of the article, or may have a limited amount of time to make a selection of a given article. In others, linguistic difficulties may contribute to improper selection and usage.

Typical instructional matter pertaining to the proper selection and use of absorbent articles conventionally comprises printed text, pictures, diagrams, labels, and combinations thereof located on the package. The objective of any optimal instructional matter is to be univocal, i.e., to convey a message regarding proper selection and usage in such a clear, concise, and exact manner that essentially any user, regardless of the package or wrapper, is prompted to choose and employ the article correctly.

Accordingly, the proper usage of extra, regular, or light capacity absorbent articles begins with the proper selection of such articles independent of the package and/or wrapper. The present invention provides an easy and intuitive signal for selecting the proper absorbency, which provides a consumer benefit and ensures that the right article is chosen.

SUMMARY OF THE INVENTION

The present invention relates to an array of disposable absorbent articles. The array comprises a first absorbent article and a second absorbent article. The first absorbent article is enclosed in a first tampon applicator comprising i.) an outer surface wherein the outer surface comprises an outer surface area and ii.) a first indicator comprising a first surface area. The first indicator is disposed on the first absorbent article and corresponds to a first absorbency. The first indicator is disposed on the first absorbent article. A second absorbent article is enclosed in a second tampon applicator comprising i.) an outer surface wherein the outer surface comprises an outer surface area and ii.) a second indicator comprising a second surface area. The second indicator is disposed on the second absorbent article and corresponds to a second absorbency. The second indicator is disposed on the second absorbent article. The first surface area of the first absorbent article is different than the second surface area of the second absorbent article.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying drawings, in which:

DETAILED DESCRIPTION OF THE INVENTION

Figure 1:
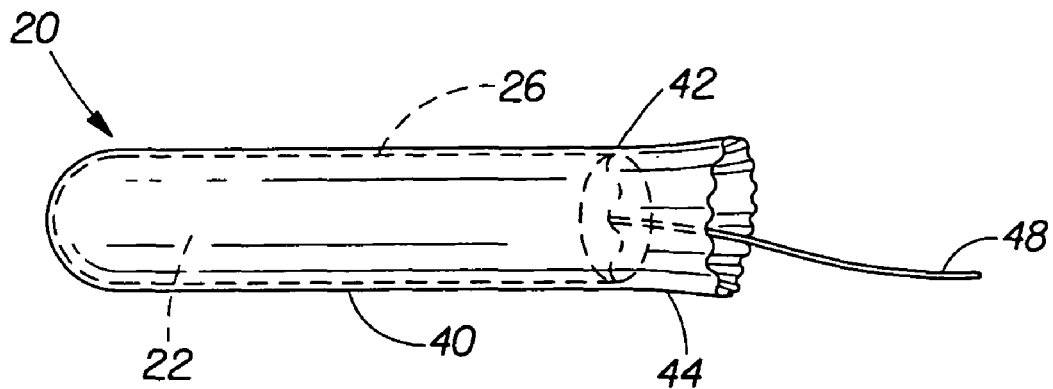
FIG. 1 is a perspective view of a tampon of the present invention incorporating a compressed absorbent member and an overwrap covering the exterior surface and forming a skirt.

Section A will provide terms which will assist the reader in best understanding the features of the invention but not to introduce limitations in the terms inconsistent with the context in which they are used in this specification. These definitions are not intended to be limiting. Section B will discuss the tampon of the present invention.

A. Terms

The following are terms which will assist the reader in best understanding the features of the invention, but do not introduce limitations in the terms inconsistent with the context in which they are used in this specification. These definitions are not intended to be limiting.

"Absorbent articles" as referred to herein are primarily sanitary napkins, sanitary panties, interlabial devices, intravaginal devices (tampons), adult incontinence products, infant diapers, pantiliners, and the like. Theses articles have been described in the extensive patent literature and many such articles are in the stream of commerce. See, for example, for sanitary napkins, U.S. Pat. No. 4,463,045 issued to Ahr et al. and U.S. Pat. No. 4,556,146 issued to Swanson et al.; for tampons, U.S. Pat. No. 5,087,239 issued to Beastall et al. and U.S. Pat. No. 5,279,541 issued to Frayman et al.; and for diapers, U.S. Pat. No. 4,573,986 issued to Minetola et al.; U.S. Pat. No. 4,695,278 issued to Lawson; U.S. Pat. No. 4,081,301 issued to Buell; and U.S. Pat. No. 4,515,595 issued to Kievit. Typically, the disclosed absorbent articles contain an absorbent structure in the form of a "core" or a pad. Various fluid-permeable topsheets, fluid-impermeable backsheets, panty-protective "wings," tape fasteners are optionally used to construct elements for such articles and are all within the experience of those of ordinary skill in the art.

The term, "surface area" as used herein refers to the measure of any two-dimensional figure within a 1 cm by 1 cm measured portion, such that two surface areas may be compared relatively to one another. While the measured portion will have a defined dimension, the surface area within that portion will always be different from the defined dimension if the tampon has topographical features such as protuberances, depressions, and grooves present within the measured portion. Any known method may be used so long as the measurement does not alter or otherwise distort the surface area, such as by swelling the materials. The preferred method of measure involves image analysis using any image analysis software or algorithm for assessing surface area. It should be understood that the surface area of interest is that which is apparent at the millimeter scale using light microscopy or macrophotography. As well, it should be noted that the surface area is not at the molecular or atomic scale, e.g. techniques such as AFM or BET are not useful herein.

As used herein, "indicator" refers to a signal perceptible to the user that corresponds to a functionally distinguishable characteristic of a feminine hygiene article. In a system of products, the functionally-distinguishable characteristic of a feminine hygiene article is a characteristic that is different in surface area from other products in the same array. The indicator can be any indicia and/or shape. As used herein, indicia is any identifying marking, which may include words and/or graphics identifying the product in use.

As used herein, "compression" refers to the process of pressing, squeezing, compacting or otherwise manipulating the size, shape, and/or volume of a material to obtain a tampon having a vaginally insertable shape. The term "compressed" refers to the state of a material or materials subsequent to compression. Conversely, the term "uncompressed" refers to the state of a material or materials prior to compression. The term "compressible" is the ability of a material to undergo compression.

As used herein, the term "density" is used with its common technical meaning with units of $g/cm^3$ or g/cc. The density may refer specifically to that of a specific region or feature of the tampon as noted. The density will be measured, unless otherwise noted, by taking the weight divided by the geometric volume described by the shape. Unless noted, density refers to that of the overall structure and not the individual components, and will include in the measurement void volume of small pores and voids within the overall structure.

The term "digital tampon" refers to a tampon which is intended to be inserted into the vaginal canal with the user's finger and without the aid of an applicator. Thus, digital tampons are typically visible to the consumer prior to use rather than being housed in an applicator.

The term "folded" as used herein, is the configuration of the tampon pledget that may be incidental to lateral compaction of the absorbent material or may purposely occur prior to a compression step. Such a configuration is readily recognizable, for example, when the absorbent material abruptly changes direction such that one part of the absorbent material bends and lies over another part of the absorbent material.

As used herein, "generally cylindrical" refers to the usual shape of tampons as is well known in the art, but which also includes oblate or partially flattened cylinders, curved cylinders, and shapes which have varying cross-sectional areas (such as a Coke™ bottle shape). The longitudinal axis refers to the longest linear dimension of the tampon. The cross-section refers to a slice taken at right angles to the longitudinal axis.

The term "joined" or "attached," as used herein, encompasses configurations in which a first element is directly secured to a second element by affixing the first element directly to the second element; configurations in which the first element is indirectly secured to the second element by affixing the first element to intermediate member(s) which in turn are affixed to the second element; and configurations in which the first element is integral with the second element; i.e., the first element is essentially part of the second element.

Figure 2:
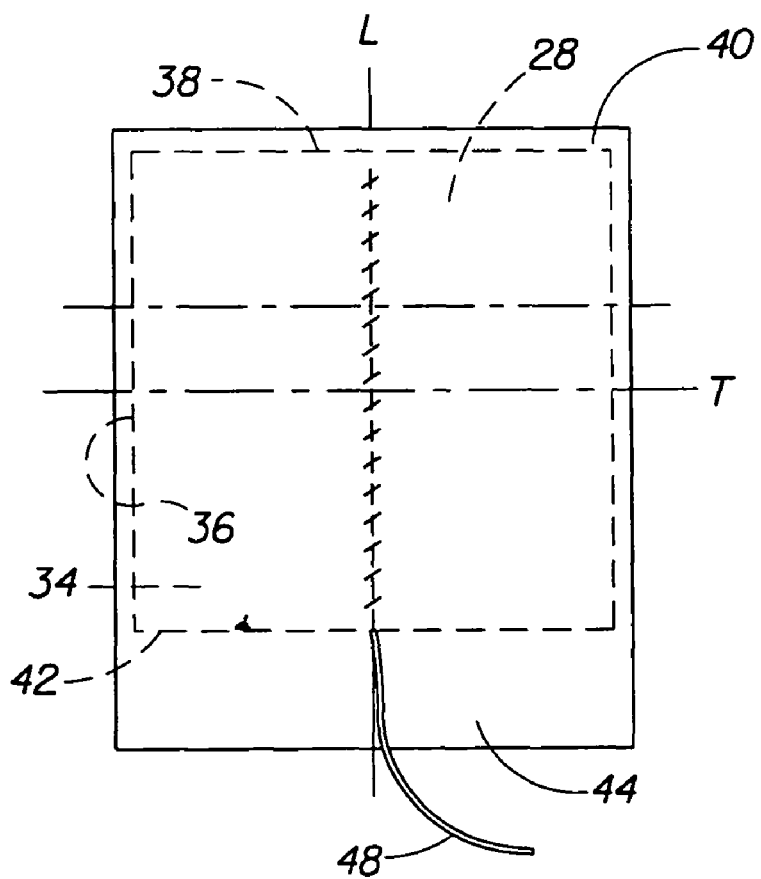
FIG. 2 is a plan view of an assembled absorbent material and overwrap prior to compression.

As used herein, the term "longitudinal axis" of a tampon refers to the axis that runs through the center of the tampon as shown in FIG. 2. A portion of the tampon may be asymmetric about the longitudinal axis, such as when the withdrawal end region is flared and distorted from the original shape of the rest of the tampon (such as a "fin shape"). Further, the longitudinal axis may be linear or non-linear.

The "outer surface" of a tampon refers to the visible surface of the (compressed and/or shaped) tampon prior to use and/or expansion. At least part of the outer surface may be smooth or alternatively may have topographic features, such as ribs, spiraling ribs, a mesh pattern, or other topographical features. Typically, tampons are constructed from an absorbent material, which has been compressed and/or shaped in any or all of the width direction, the radial direction, and the axial direction, in order to provide a tampon which is of a size and stability to allow insertion within the vagina or other body cavity.

The term "cross-section," as used herein, is any 5 mm thick section orthogonal to the longitudinal axis.

As used herein, the terms "pledget" or "tampon pledget" are intended to be interchangeable and refer to a construction of absorbent material prior to the compression and/or shaping of such construction into a tampon as described above. Pledgets may be rolled, folded or otherwise manipulated prior to compression. Tampon pledgets are sometimes referred to as tampon blanks, or a softwinds, and the term "pledget" is intended to include such terms as well. In general in this specification, the term "tampon" is used to refer to a finished tampon after the compression and/or shaping process. It will be recognized by those of skill in the art that in some contexts these terms are interchangeable. The different stages of tampon manufacture are described herein with an eye toward providing the greatest possible clarity. Therefore, the terms used are to assist the reader in best understanding the features of the invention and not to introduce limitations in the terms not consistent with the context in which they are used in this specification.

As used herein, a tampon has a "self-sustaining shape" when a tampon pledget has been compressed and/or shaped such that it assumes a general shape and size, which is vaginally insertable, absent external forces. It will be understood by one of skill in the art that this self-sustaining shape need not, and preferably does not persist during actual use of the tampon. That is, once the tampon is inserted and begins to acquire fluid, the tampon may begin to expand and may lose its self-sustaining form.

As used herein, the term "tampon" refers to any type of absorbent structure that can be inserted into the vaginal cavity or other body cavities for the absorption of fluid therefrom or for the delivery of active materials, such as medicaments or moisture. A tampon can be straight or non-linear in shape, such as curved along the longitudinal axis.

Generally, there are two types of tampons. The first type of tampon is a self-sustaining tampon. Tampons are generally "self-sustaining" in that they will tend to retain their general shape and size before use. A typical self-sustaining tampon is 35-60 mm long, the length measured from the top of the tampon to the base of the tampon along a longitudinal axis. The measurement to the base of the tampon does not include any overwrap, secondary absorbent member, or withdrawal cord which extends beyond the tampon's main absorbent material. A typical self-sustaining tampon is 5-20 mm wide corresponding to the largest cylindrical cross section. The width can vary along the length of the self-sustaining tampon.

The second type of tampon is an easily "deformable, fluid-permeable bag tampon". The deformable, fluid-permeable bag tampon consists of, but is not limited to, pieces such as absorbent chips, spheres, or fibers such that the fluid permeable bag tampon is readily deformable with a force of less than about 3 psi. The tampon is substantially deformable at pressures of less than about 1 psi; resulting in the tampon spreading or being easily indented when the pressure is applied from a surface of about 0.15 mm diameter.

As used herein, "tampon applicator" refers to a device or implement that facilitates the insertion of a tampon, medicament, treatment device, visualization aid, or other into an external orifice of a mammal, such as the vagina, rectum, ear canal, nasal canal, or throat. Non-limiting specific examples of such include any known hygienically designed applicator that is capable of receiving a tampon may be used for insertion of a tampon, including the so-called telescoping, tube and plunger, and the compact applicators, an applicator for providing medicament to an area for prophylaxis or treatment of disease, a spectroscope containing a microcamera in the tip connected via fiber optics, a speculum of any design, a tongue depressor, a tube for examining the ear canal, a narrow hollow pipe for guiding surgical instruments, and the like.

The term "transparent" refers to the material capability of transmitting light so that the component, or a portion thereof, can be seen as clearly as if there were no intervening material between the component and the perceiver. Furthermore, the "transparent" clarity indicates the degree of distortion of an object that can be seen through a film. (See The Wiley" Encyclopedia of packaging technology). The material for the tampon applicator 60 is transparent or "substantially transparent" when light readily passes through, such that the indicator 21 placed on the tampon 20 located opposite the transparent material can be viewed by the naked eye. The tampon applicator 60 can be "substantially transparent" when the window is frosted or not frosted in a matte or gloss finish. When the product (i.e. tampon applicator) is frosted or not frosted in a matte or gloss finish, the frost or color can be any colors such as selected from the group consisting of blue, yellow, green, pink, white, orange, gold, rust, gray, brown, violet, and mixtures thereof.

As used herein, the terms "vaginal cavity" and "within the vagina" refer to the internal genitalia of the human female in the pudendal region of the body.

B. General Description of Basis Parts of a Tampon

FIG. 1 shows a general tampon 20. The tampon 20 can be any shape in the art and any type of tampon known in the art. In one non-limiting example, tampon 20 could be a shaped tampon 20, such as that disclosed in U.S. Pat. No. 6,824,536. FIG. 1 illustrates a tampon 20 for feminine hygiene.

Referring to FIGS. 1-2, in general, tampon 20 comprises a compressed absorbent member 22 which comprises absorbent material 28 and a fluid permeable overwrap 40 that covers absorbent member 22. Overwrap 40 may extend beyond one end of absorbent member 22 to form a skirt portion 44. A removal means, such as string 48 can be provided to facilitate removal of the tampon 20 after use. Tampons, including overwraps for use as the body contacting surface thereof, are well known in the art and need no detailed description of various alternative and optional designs.

Each major element of the tampon 20 is described below.

a. Absorbent Material

Referring to FIG. 2, the absorbent material 28 may be any suitable size and thickness suitable for compression into a tampon 20 (FIG. 1) having a vaginally insertable shape. In the embodiment shown in FIG. 2, the absorbent material 28 is generally square or rectangular, but other shapes such as trapezoidal, triangular, hemispherical, chevron and hourglass shaped are also acceptable. A more detailed description of liquid-absorbing materials and pledget shapes and dimensions can be found in currently pending and commonly assigned, U.S. patent Ser. No. 10/039,979, filed Oct. 24, 2001, entitled "Improved Protection and Comfort Tampon,"

to Agyapong, et al. A typical size for absorbent material 28 prior to compression may be from about 40 mm to about 100 mm in length and from about 40 mm to about 80 mm in width. The typical range for the overall basis weight is from about 150 gsm to about 1200 gsm.

The absorbent material 28 may be a laminar structure comprised of integral or discrete layers. In other embodiments, the absorbent material 28 need not have a layered structure at all. If the compressed absorbent material 28 of the present invention is layered, the layers may comprise different materials. For example, in one embodiment, the outer layers may comprise primarily rayon, while the intermediate layer or layers may comprise primarily cotton. Optionally, the entire compressed absorbent material 28 may comprise a uniform or non-uniform blend of materials throughout. In one layered embodiment, each of the layers may comprise essentially 100% of the same material, such as outer layers of 100% rayon and an intermediate layer of 100% cotton. A Super Plus absorbency tampon of the present invention may be made from a pledget comprising about 100% rayon fibers. A Super absorbency or regular absorbency tampon of the present invention may be made from a pledget comprising about 25% cotton and about 75% rayon fibers. A Junior absorbency tampon may be made from a pledget comprising about 50% cotton and about 50% rayon fibers.

The absorbent material 28 may comprise a folded structure or may be rolled. The resulting compressed absorbent member 22 (FIG. 1) of the tampon 20 may be constructed from a wide variety of liquid-absorbing materials commonly used in absorbent articles such as rayon (including tri-lobal and conventional rayon fibers), cotton, or comminuted wood pulp which is generally referred to as airfelt. Examples of other suitable absorbent materials 28 include creped cellulose wadding; meltblown polymers including coform; chemically stiffened, modified or cross-linked cellulosic fibers; synthetic fibers such as crimped polyester fibers; foam; tissue including tissue wraps and tissue laminates; or any equivalent material or combinations of materials, or mixtures of these.

Typical absorbent materials 28 comprise cotton, rayon folded tissues, woven materials, non-woven webs, synthetic and/or natural fibers or sheeting. The tampon 20 and any component thereof may comprise a single material or a combination of materials. Additionally, superabsorbent materials, such as super polymers or absorbent gelling and open-celled foams materials may be incorporated into the tampon.

The materials for the tampon 20 can be formed into a fabric, web, or batt that is suitable for use in the absorbent material 28 by any suitable process such as airlaying, carding, wetlaying, hydroentangling, needling or other known techniques.

In another non-limiting embodiment, the absorbent material 28 and resulting compressed absorbent member 22 (FIG. 1) comprise rayon, cotton, or combinations of both materials. These materials have a proven record of suitability for use in the human body. The rayon used in the absorbent material 28 may be any suitable type typically used in disposable absorbent articles intended for in vivo use. Such acceptable types of rayon include GALAXY Rayon (a tri-lobed rayon structure) available as 6140 Rayon from Acordis Fibers Ltd., of Kelheim, Germany. SARILLE L rayon (a round fiber rayon), also available from Acordis Fibers Ltd. is also suitable. Any suitable cotton material may be used in the compressed absorbent member 22 (FIG. 1). Suitable cotton material includes, long fiber cotton, short fiber cotton, cotton linters, T-fiber cotton, card strips, and comber cotton. Preferably, the cotton layers should be scoured and bleached cotton absorbent with a glycerin finish, or other suitable finish. Other materials that may be incorporated into the tampon pledget including comminuted wood pulp which is generally referred to as airfelt, folded tissues, woven materials, nonwoven webs, peat moss, absorbent foams (such as those disclosed in U.S. Pat. No. 3,994,298 issued to DesMarais on Nov. 30, 1976 and U.S. Pat. No. 5,795,921 issued to Dyer, et al.,) capillary channel fibers (such as those disclosed in U.S. Pat. No. 5,356,405 issued to Thompson, et. al on Oct. 18, 1994), high capacity fibers (such as those disclosed in U.S. Pat. No. 4,044,766 issued Kaczmarzk, et al. on Aug. 30, 1977), superabsorbent polymers or absorbent gelling materials (such as those disclosed in U.S. Pat. No. 5,830,543 issued to Miyake, et al. on Nov. 3, 1998).

Pressures and temperatures suitable for compression are well known in the art. Typically, the absorbent material 28 and the overwrap 40 are compressed in the radial direction and optionally axially by any means well known in the art. While a variety of techniques are known and acceptable for these purposes, a modified tampon compressor machine available from Hauni Machines, Richmond, Va., is suitable.

The fibrous material of the tampon 20 of the present invention may have uniform density over a cross section of the tampon 20. Alternatively, fibrous material of the tampon 20 may have varying density over a cross section of the tampon 20. A tampon 20 having varying densities is described in greater detail in co-pending patent application filed Nov. 4, 2003, entitled "Substantially Serpentine Shaped Tampon with Varying Density Regions", to Almond, and co-pending patent application filed Nov. 4, 2003, entitled "Substantially Serpentine Shaped Tampon with Varying Density Regions", to Almond.

b. Overwrap

Referring to FIG. 2, in the embodiments shown, the overwrap material 40 is generally rectangular, but other shapes such as trapezoidal, triangular, hemispherical, chevron, hourglass shaped, "T" and "L" shaped are also acceptable. Optimally, the overwrap 40 may correspond to the shape of the absorbent material 28. The overwrap 40 is positioned around the absorbent material 28 so that the overwrap 40 may be proximate with the insertion end 38 of the absorbent material 28. In this regard, the overwrap 40 could exactly match up to the insertion end 38 or could for example extend from about 2 mm to about 8 mm over the insertion end 38. As well, the overwrap 40 may extend beyond the withdrawal end 42 to form a skirt portion 44 as discussed below.

Because the overwrap 40 can be wrapped in the various configurations, the width of the overwrap 40 may vary. The width of the overwrap 40 may be wider or less wide than the measure of the longitudinal or transverse axis of the absorbent material 28 it is being wrapped around.

The overwrap 40 substantially covers both the first surface 34 and the second surface 36 of the absorbent material 28. "Substantially covers" in this case means that the overwrap 40 covers at least about 75%, optionally at least about 90% of the combined surface area of the first surface 34 and the second surface 36. The overwrap 40 may be wrapped around the longitudinal axis "L" or the transverse axis "T" as shown in the attached figures in another embodiment. As well, two or more separate pieces of overwrap 40 can sandwich the absorbent material 28.

The overwrap 40 may be joined to the absorbent material 28 by any variety of means. The overwrap 40 may be joined to itself or to the absorbent material 28. For example, one portion of overwrap 40 may be joined to an opposed portion of the overwrap 40 or the absorbent material 28 using any suitable adhesive or heat/pressure bonding means. Such adhesive may extend continuously along the length of attachment or it may be applied in a "dotted" fashion at discrete intervals. One method of heat bonding includes thermally bonding, fusion bonding, or any other suitable means known in the art for joining such materials. Alternatively, the overwrap 40 may be joined to the absorbent material 28 along with the withdrawal cord 48 by sewing as shown in FIG. 2. Such sewing may use natural or synthetic thread.

The material of the overwrap 40 may comprise materials such as rayon, cotton, bicomponent fibers, polyethylene, polypropylene, other suitable natural or synthetic fibers known in the art, and mixtures thereof. The tampon 20 may have a nonwoven overwrap comprised of bicomponent fibers that have a polypropylene core surrounded by polyethylene manufactured by Vliesstoffwerke Christian Heinrich Sandler GmbH & Co. KG (Schwarzenbach/Saale, Germany) under the tradename SAS B31812000. The tampon 20 may comprise a nonwoven overwrap of a hydroentangled blend of 50% rayon, 50% polyester available as BBA 140027 produced by BBA Corporation of South Carolina, U.S. The overwrap may be 100% polyester. The overwrap 40 may be treated to be hydrophilic, hydrophobic, wicking or non-wicking. The tampon pledget may also contain a variety of other adjuvants such as odor control agents, antibacterial agents, colorants, indicators for various kinds of illnesses such as yeast infections, indicator features for signaling when the tampon should be changed, and the like.

c. Skirt Portion/Secondary Absorbent

Referring to FIG. 2, the overwrap 40 may extend beyond the withdrawal end 42 to form a skirt portion 44. The length of the skirt portion 44 is not critical. Typically, the overwrap 40 can extend from about 2 mm to about 30 mm beyond the withdrawal end 42 of the absorbent material 28. Typically, the overwrap 40 extends from about 5 mm to about 20 mm beyond the withdrawal end 42 of the absorbent material 28. In one embodiment, the skirt portion 44 may not be compressed.

Referring to FIG. 1, both the compressed absorbent member 22 and skirt portion 44 of the overwrap 40 may reside entirely within the vaginal cavity of the wearer during use of the tampon 20. This is achieved by the relative closeness of the skirt portion 44 to the withdrawal end 42 of the absorbent material 28 as well as of the relative size compared to the overall size of the tampon 20. In particular embodiments, only the withdrawal cord 48 or other withdrawal means resides externally to the orifice of the vagina.

The tampon of the present invention may comprise a secondary absorbent member such as that disclosed in U.S. Pat. Nos. 6,258,075 and 6,599,279.

d. Optional Components

Referring to FIG. 1, optionally, the tampon of the present invention could include an additional overwrap 40 that is non-aggressive. This additional overwrap 40 would substantially cover the overwrap 40 that substantially covers the exterior surface 26 of the compressed absorbent member 22 of the tampon 20. The additional overwrap 40 need only extend as to be proximate with the withdrawal end 42 of the absorbent material 28 so that the entire skirt portion 44 of the tampon 20 is left uncovered by the additional overwrap 40. This additional overwrap 40 could be added prior to or subsequent to compression.

In one embodiment, the tampon 20 of the present invention may comprise a withdrawal member 48. The withdrawal member 48 could be joined to the tampon 20 and graspable for digital removal after use. The withdrawal member 48 may be joined to at least the primary compressed absorbent member 22 and extends beyond at least the withdrawal end 42. The withdrawal member 48 may be attached in any suitable manner known in the art including sewing, adhesive attachment, bonding, thermal bonding, or a combination thereof including the method disclosed in currently pending, commonly assigned, U.S. patent application Ser. No. 10/610,075, filed Jun. 30, 2003, entitled "Method and Apparatus for Cord Attachment" to Sargent, et al. The withdrawal member 48 may be joined to any suitable location on the tampon.

Any of the withdrawal members 48 currently known in the art may be used as a suitable withdrawal mechanism. In addition, the withdrawal member 48 can take on other forms such as a ribbon, loop, tab, or the like. The withdrawal member 48 may be integral with the absorbent material 28 (FIG. 2). Withdrawal member 48 useful in the present invention may be made of any suitable material known in the prior art and include cotton and rayon. The withdrawal member 48 or regions of the withdrawal member 48 may be treated to be non-absorbent, absorbent or hydrophilic.

C. General Description of Basis Parts of a Tampon Applicator

Figure 11:
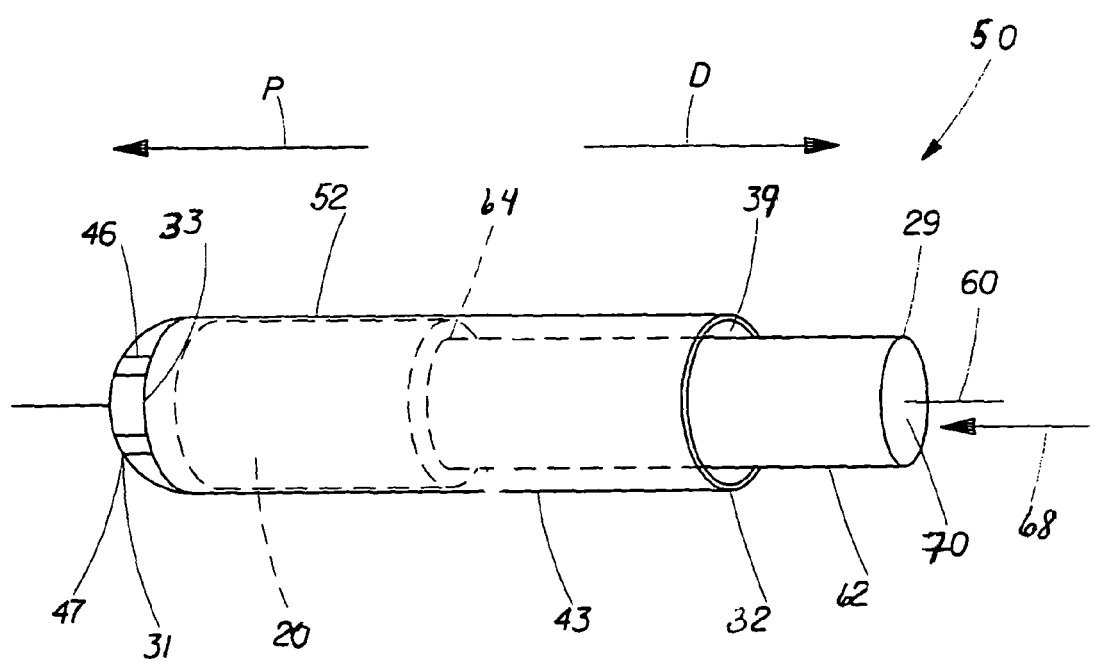
FIG. 11 is a perspective view along a longitudinal axis of a tampon applicator of the present invention.
Figure 12:
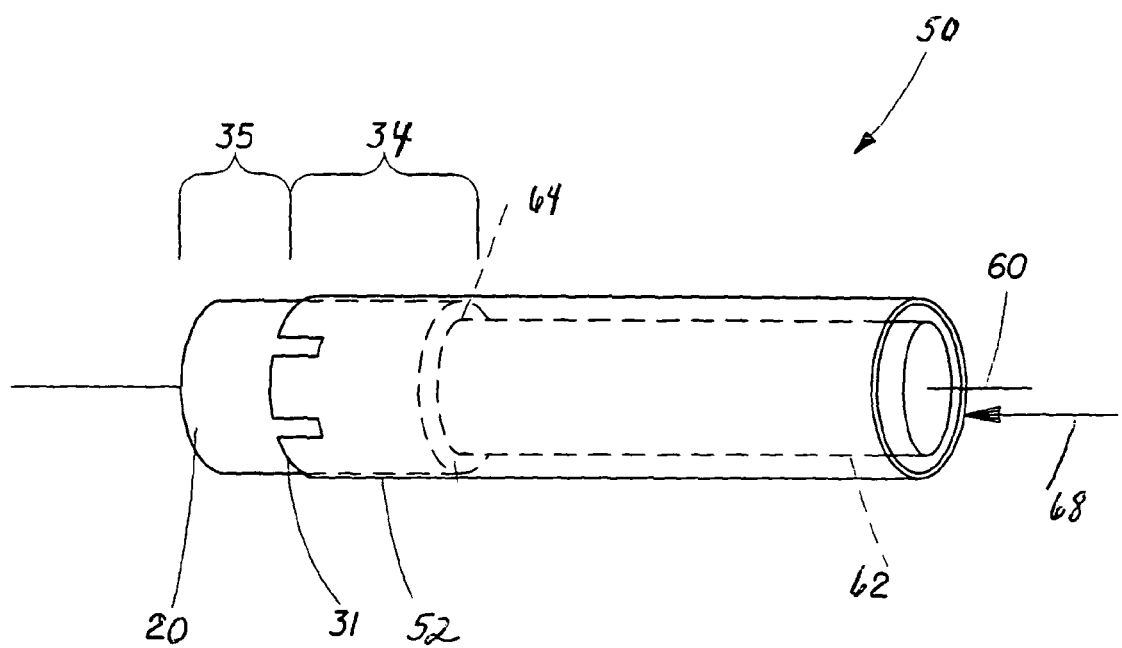
FIG. 12 is a perspective view of the tampon applicator of the present invention when the tampon applicator is fully engaged.

Referring to FIG. 11, a tampon applicator 50 is shown which is designed to position tampon 20 inside the vaginal cavity. Also, FIG. 11 shows "proximal" and "distal" designated as P and D, respectively. The tampon applicator 50 may be used with any type of tampon 20. The tampon 20 could be a self-sustaining tampon or a deformable fluid permeable bag tampon.

Generally, the tampon applicator 50 includes an outer member 52 and an inner member 62. The outer member 52 comprises an insertion end 31 and a second end 32 opposed to the insertion end 31. During insertion of the tampon applicator 50 into the body of a wearer, the insertion end 31 is the most proximal end to the body of the wearer along the longitudinal axis 60 and the second end 32 is the most distal end to the body of the wearer along the longitudinal axis 60. A preformed hinge or groove 33 may extend around the periphery of the outer member 52 near the insertion end 31. The outer member 52 may also have a dome-shaped end having a number of radial slits 46 therein extending from a central aperture to the groove 33. The portion of the outer member 52 adjacent to the insertion end 31 may also have an openable end, such as petals 47. In addition, the outer member 52 can contain a grip region 43 located adjacent to the second end 32 of the outer member 52.

The inner member 62 is dimensioned to slidably move within the hollow interior portion 39 of the outer member 52, with minimal clearance therebetween. The inner member 62 has a first end 64 and a second end 29 opposed to the first end 64. The first end 64 is the most proximal end of the inner member 62 along the longitudinal axis 60. In this embodiment, the first end 64 provides the necessary force to expel the tampon 20. The second end 29 is the most distal end of the inner member 62 along the longitudinal axis 60. An axial force 68 is applied to the second end 29 of inner member 62 to expel the tampon 20. Also, the inner member 62 can have a hollow interior portion 70. Alternatively, the inner member 62 can be solid or partially solid.

The tampon applicator 50 has a pre-expelled state and a partially expelled state. During the pre-expelled state, as is readily seen in FIG. 11, the tampon 20 sits within the outer member 52 and is substantially aligned with the tampon applicator 50. The tampon 20 can remain snugly therein without any outside force to sustain its position in the tampon applicator 50.

Figure 13:
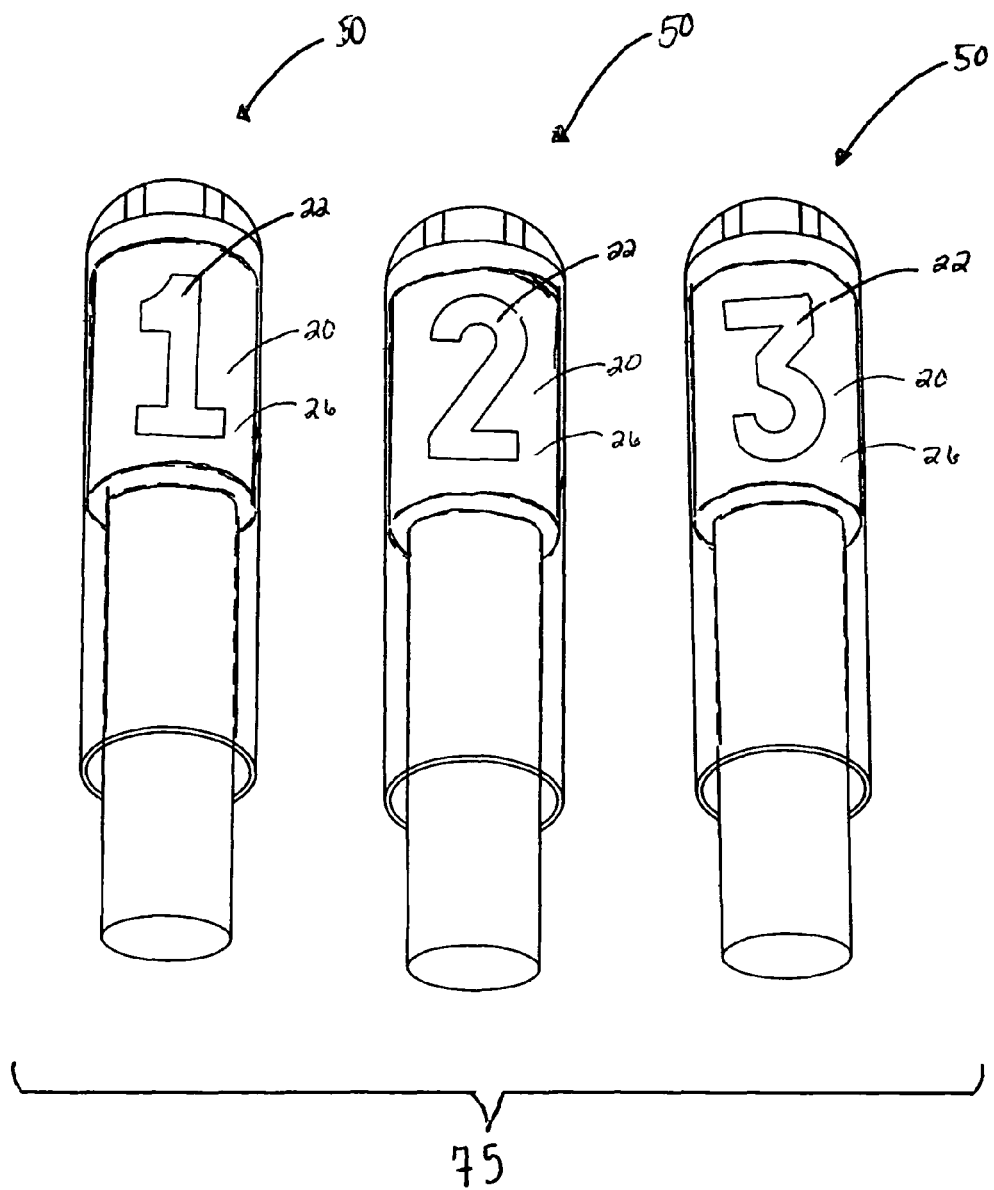
FIG. 13 is a view of an array of feminine hygiene articles of the present invention.

As is readily seen in FIG. 13, when the axial force 68 is applied along the longitudinal axis 60, the inner member 62 slides toward the insertion end 31 of the outer member 52. The inner member 62 bears against the rear end of tampon 20 pushing the tampon 20 toward the insertion end 31 of outer member 52. Upon full engagement of inner member 62 with outer member 52, the exposed portion 35 of the tampon 20 is expelled from the tampon applicator 50 and a remaining portion 37 of the tampon 20 is contained within the tampon applicator 50.

D. Incorporation of Indicators into Tampons

The above disclosure is meant to give a general description of the basic parts of feminine hygiene articles such as tampons and the like as they are known in the art. The description is not intended to be limiting. Any and all of various known elements, features and processes of known tampons and the like can be incorporated in the feminine hygiene article of the present invention as desired or needed for particular use benefits. Now, with respect to the remaining disclosure, the novel features and benefits of the present invention will be described.

In its broadest aspect, the present invention is directed to an array of disposable absorbent articles comprising a line-up of disposable absorbent articles in which each disposable absorbent article comprises an indicator. When so employed, the surface area that the indicator covers provides an easy and intuitive method for indicating the absorbency of the product. When indicators are placed on the tampon, the indicator provides a method for selecting the proper absorbency products independent of the package. Thus, when the article is then removed from the original container and placed in the bathroom drawer, purse, etc. the user can select the proper absorbency product.

By the present invention, a system of distinct indicators is used to implement the proper selection and use of consumer products, including catamenials, especially tampons, sanitary napkins, and interlabial devices. The present invention may also be used in other fields such as beauty care, food and beverage, health care, laundry and cleaning, and tissues and towels. For example, indicators may be used in beauty care to denote product performance characteristics such as more or less moisture; in coffee products to differentiate between light, medium, and dark roast levels; in the health care area to denote stronger medicine such as cough drops and chloraseptics; in laundry and cleaning to indicate a higher concentration of detergent; and in tissues and towels to denote levels of absorbency. The use of indictors in this manner univocally and unequivocally connotes performance characteristics, thereby improving user satisfaction with the product and decreased anxiety in choosing the correct product.

The indicators are perceived and referred to in terms of the amount of surface area that is covered by the tampon. Typically, the more surface area that the indicator covers the greater the absorbency that the indicator indicates. For example, in the context of one embodiment the present invention, a tampon having six grooves signals a "mini" absorbency tampon; a tampon having nine grooves signals a "normal" absorbency tampon; a tampon having twelve grooves signals a "super" absorbency tampon, and a tampon having fifteen grooves signals a "super plus" absorbency tampon. It will be appreciated by those skilled in the visual arts that the number of grooves are relative, not absolute, terms that can be used to compare the surface areas with each other.

With such a line up, the consumer is able to remember easily that less surface area corresponds to lower absorbency while higher absorbency corresponds to a higher surface area. Preferably, the variation in surface area is great enough to be readily perceived by a consumer without having to refer to an external basis or calibration means for comparison. For example, if the product performance characteristic being represented is absorbency, an indicator covering about 24% of the surface area of the tampon might represent low absorbency. An indicator covering about 46% of the surface area of the tampon might represent high absorbency, while an indicator covering about 41% of the surface area of the tampon might represent regular absorbency.

Figure 3:
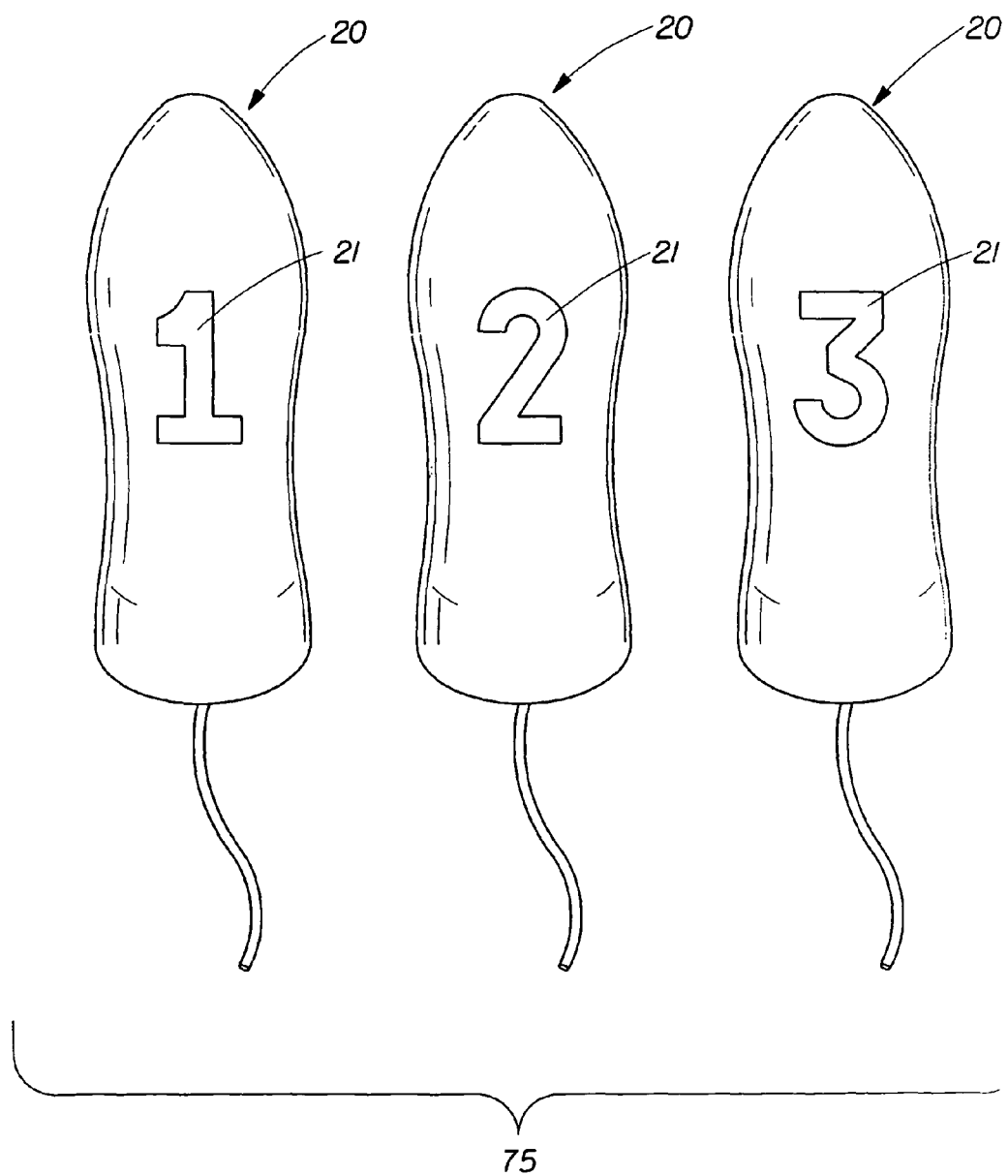
FIG. 3 is a view of an array of feminine hygiene articles of the present invention.

Referring to FIG. 3, the indicators 21 may encompass the entire tampon 20 or may encompass part of the tampon 20. For example, the indicators 21 may encompass one-fourth of the surface area of the tampon 20. In yet another example, the indicators 21 may encompass two-thirds of the surface area of the tampon 20.

The indicators 21 may be placed anywhere on the tampon 20. In other words, the overall trade dress of the product may use the indicators 21 in a variety of ways. Specifically, the indicators 21 may be placed anywhere on the tampon 20, e.g., on the top, sides, or bottom, or all three.

Referring to FIG. 1, the indicators 21 (FIG. 3) can be placed on the overwrap 40, absorbent material 28, the skirt 44, on another portion of the tampon 20 as long as it is visually perceptible to the user, or on any combination of the components of the tampon 20. Referring to FIG. 2, for example, indicators 21 (FIG. 3) may be placed on the absorbent material 28. In yet another non-limiting example, indicators 21 (FIG. 3) may be placed on the absorbent material 28 and the overwrap 40. In yet another non-limiting example, indicators 21 (FIG. 3) may be placed on the absorbent material 28, the overwrap 40, and the skirt 44.

Referring to FIG. 3, indicators 21 may be visually perceptible by techniques including, but not limited to, printing, stamping, coating, impregnating, embossing, folding, any known process that makes a visual, or even tactile, impression that indicates the indicator 21 having a surface area, or any combinations thereof. Various printing methods may be used to impart indicators 21 including, but not limited to, letterpress, flexography, gravure, offset lithography, screen, and inkjet. Indicators 21 can comprise printed indicia, such as ink-jet-printed figures, designs, lines or line segments, or embossed ridges or bumps, folds, pleats, or any other means known in the art for providing visible indications that impart an indictor 21 which covers the surface area of the tampon 20 and aids the user in choosing the proper absorbency tampon from a line-up of tampons.

Indicators 21 can be any size or shape. Indicators 21 can be any size as long as the indicator 21 is able to be readily perceived by a consumer without having to refer to an external basis or calibration means for comparison. The indicator 21 can be circular, square, rectangular, triangular, arced, curved, or any other conceivable shape possible as long as the indicator 21 is able to be readily perceived by a consumer without having to refer to an external basis or calibration means for comparison. While the indicators 21 can be a wide range of shapes, it is preferred to use a member selected from the group consisting of straight grooves, spiral grooves, flower petals, ellipses, and mixtures thereof.

The indicator(s) 21 may be formed to have essentially identical size and shape as compared to other indicators 21 on the individual tampon 20. In one non-limiting example, the tampon has twenty indicators shaped like protuberances. Each protuberance is identical to the other protuberances. Alternatively, the indicator 21 may be formed to have various sizes and shapes as compared to another indicator 21 on the tampon 20. In one non-limiting example, the tampon may have twenty indicators. However, each indicator may have a different geometric shape. Additionally, each indicator may have a different size.

The number of indicators 21 and the distance over which the indicators 21 extend may vary. The number of indicators 21 may range from about 1 to about 50. Either an even or an odd number of indicators 21 can be present. For ease of manufacturing, it is preferred that the indicators 21 be equally spaced relative to one another. The indicators 21, however, may be unequally spaced relative to one another.

The distance between each indicator 21 depends upon the area of the tampon 20 and the size and number of indicators 21.

Indicators 21 may be arranged randomly or in a pattern. For example, indicators 21 can be arranged to form any three-dimensional geometric pattern known including but not limited to diagonal lines, straight lines, checkerboard, flowers, ovals, circles, rectangles, trapezoids, triangles, cones, alphabet letters, and mixtures thereof. Alternatively, indicators 21 may be randomly arranged so that the multiplicity of indicators 21 may comprise merely a surface roughness in no apparent pattern. In addition, indicators 21 may be arranged such that the areas between the indicators 21 may form any geometric pattern known including but not limited to flowers, ovals, circles, rectangles, trapezoids, triangles, cones, alphabet letters, and mixtures thereof.

The indicator 21 may be formed to have essentially identical size and shape as compared to other indicators 21 in the same line-up. Moreover, while the use of increasing surface area, especially those having differing intensities, can be used to signal absorbency or other product performance characteristic such as size and strength, it is preferred to use differing surface areas which have indicators 21 of the same basic shape. For example, over the range of absorbencies: one groove which covers 10% of the surface area of the tampon can signal light absorbency; two grooves which covers 30% of the surface area of the tampon can signal regular absorbency; and three grooves which covers 60% of the surface area of the tampon can signal extra absorbency.

Alternatively, the indicator 21 may be formed to have various sizes and shapes as compared to another indicators 21 in the same line-up. In other embodiments, the indicators 21 may have shapes which are not similar as long as the indicators 21 on each tampon 20 have an increased surface area which correlates with the increased absorbency. An important advantage of using a range of surface areas within the line-up is that continuity for the visual selection of the overall product line is maintained, while the user is provided with the desired intuitive selection, and usage means which is the object of this invention.

Referring to FIG. 3, in another embodiment, feminine hygiene articles, such as tampons 20, can have indicators 21 that provide direct information-bearing signals to the user, such as numerals or written indicia that communicate information by way of clearly understood gradations in scale. For example, as shown in FIG. 3, an array 75 of tampons 20 can be identified by a number, with increasing numbers indicating an increase in a functional characteristic. For example, increasing numbers can signal an increasing amount of absorbent capacity relative to lower-numbered articles. As shown in FIG. 3, for example, the article on the far right numbered with the numeral "3" can have more absorbent capacity than that of the article in the middle numbered with the numeral "2". Other indicators 21 could be used for a more aesthetic appearance.

Figure 4:
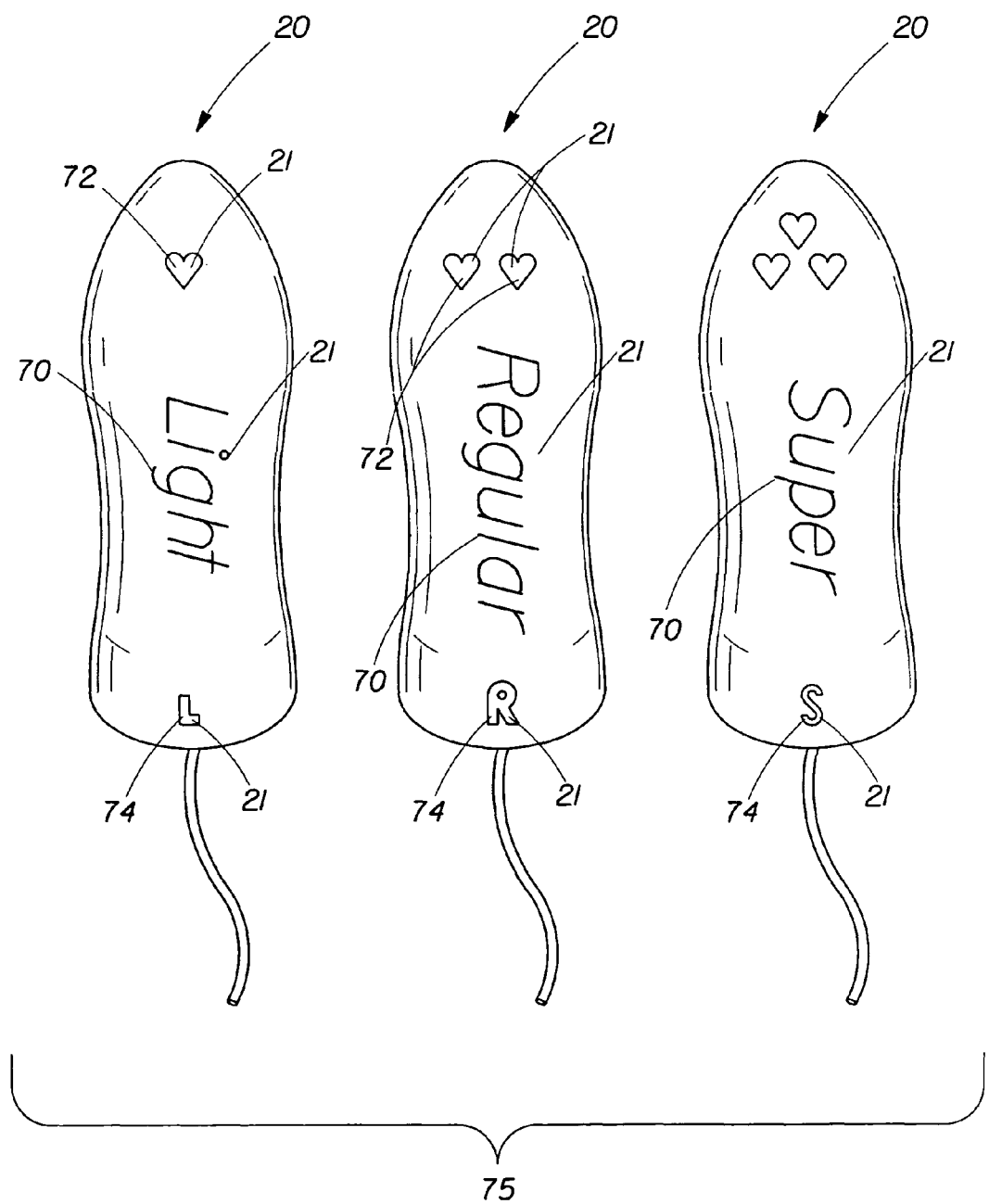
FIG. 4 is a view of an array of feminine hygiene articles of the present invention.

FIG. 4 shows an array 75 of tampons 20 having a plurality of indicators 21. As shown, each tampon 20 can have information-bearing written indicia 70 to literally "spell out" the functional characteristic, such as light absorbency, regular absorbency, or super absorbency capacity. In addition, or separately, an array of tampons 20 can be differentiated by the number of visually distinct pattern elements 72 such as the heart shapes shown in FIG. 4. Thus, the greater number of hearts, the greater the characteristic signaled by the indicator 21. In addition, or separately, the indicator 21 can include a shortened form of the information-bearing written indicia 74, such as "L" for light absorbency, "R" for regular absorbency, and the "S" for super absorbency.

In each case of the embodiments of the present invention shown in the FIGS., one benefit to the user is the identification in an array of products of differing functional characteristics, the product or products the user can choose for her particular needs. Further, another benefit to the user is the ability to take visual notice after use of a product to identify the product for future use. Thus, a user may use the middle tampon shown in FIG. 4, for example, and find that it is perfect for her needs. Upon removing the tampon she has direct visual reinforcement as to which tampon of all the various kinds it is. This enables her to easily replace it with a like tampon without having to remember what kind of tampon she used. For this reason, it may be desirable to place indicators 21 near the tampon periphery, such as pattern elements 72 or written indicia 74, such that the fluid absorbed in the tampon 20 during use does not alter or mask the indicator 21.

In a preferred mode, the product herein is displayed in a manner such that the consumer's attention is drawn to the entire product line. The product line may contain two or more products. Thus, on a store shelf or display rack, the products have the gradation of absorbencies preferably placed in a side-by-side array, most preferably in ascending order of absorbency. The ascending order may be from left to right; right to left; up to down; down to up; horizontally; or diagonally. It is noted that side-by-side herein means that all articles in the product line are in sufficient proximity to each other, either horizontally, vertically, or diagonally to be within the consumer's zone of perception at the same time. The products should be in close enough proximity to prevent undue confusion for the consumer. Thus, in a horizontal display reading from left-to-right, products having low absorbency (indicators covering less surface area), medium absorbency (indicators covering more surface area than the low absorbency tampon but the indicators covering less surface area coverage than the high absorbency tampon), and high absorbency (indicators covering more surface area than the medium absorbency tampon) are displayed together. This not only draws attention to the entire product line, but also provides additional visual signals to the consumer by virtue of the side-by-side display.

E. Tampons Enclosed in a Tampon Applicator

Referring to FIG. 11, the insertion of the tampon 20 may be aided through the use of any tampon applicator 50 adapted from the prior art. The tampons 20 of the present invention can optionally be placed in the above described tampon applicator 50. Prior art applicators having a typical "tube and plunger" type arrangement may be plastic, paper, or other suitable material. Additionally, a "compact" type applicator is also suitable. Where the tampon 20 of the present invention is shaped and provides aesthetic appeal to consumers, it is may be desirable to combine the shaped tampon with an applicator type which enables the user to observe at least a portion or the whole shape of the shaped tampon 20 and/or the indicator 22.

Referring to FIG. 13, for example, feminine hygiene articles, such as tampons 20, can have indicators 22 that provide direct information-bearing signals to the user, such as numerals or written indicia that communicate information by way of clearly understood gradations in scale. For example, as shown in FIG. 13, an array 75 of transparent tampon applicators 50 can have tampons 20 enclosed therein. In another non-limiting example, the tampon applicators can be "substantially transparent" such that the color of the tampon applicator has a blue frost. In this non-limiting example, the indicators on the tampon are still visible. The indicators 22 disposed on the tampons 20 can be viewed by the naked eye because the tampon applicators 50 are transparent. The tampons 20 can be identified with an indicator 22 disposed on the tampon 20 by a number 1, with increasing numbers indicating an increase in a functional characteristic. For example, increasing numbers can signal an increasing amount of absorbent capacity relative to lower-numbered. As shown in FIG. 13, for example, the article on the far right numbered with the numeral "3" can have more absorbent capacity than that of the tampon 20 enclosed in the tampon applicator 50 in the middle numbered with the numeral "2". Other indicators 22 could be used for a more aesthetic appearance.

The tampon applicator 50 can enclose the tampon 20 in a loose, conforming, tightly conforming and mixtures thereof tampon applicator 50 to the exterior surface 26 of the tampon 20 in order to visually show the consumer the tampon 20 with the indicator 22 enclosed therein. As stated above, tightly conforming tampon applicators 50 are particularly useful when the tampons 20 are shaped. The tampon applicators 50 should substantially enclose each individual tampon 20. "Tightly conforming," means that there is substantially no visually noticeable void space between the tampon applicator 50 and the tampon 20.

Two techniques which allow the user to better notice the shape of the tampon 20 and/or the indicator 22 are to either make visual observation possible through the use of a translucent or even transparent applicator materials, or to provide a tampon applicator insertion end that better follows and hence better displays the profiled shape of the enclosed shaped tampon than the typical commercial tampon applicators comprising straight-walled cylindrical inserter tubes often made from molded plastic or laminated cardboard tubes. These techniques may be found in currently pending and commonly assigned, U.S. patent application Ser. No. 10/150,055, filed Mar. 18, 2002, entitled "Shaped Tampon," to Kollowitz, et al.

F. Examples

The following Example illustrates the practice of the invention, but is not intended to be limiting thereof.

Example I

Figure 5:
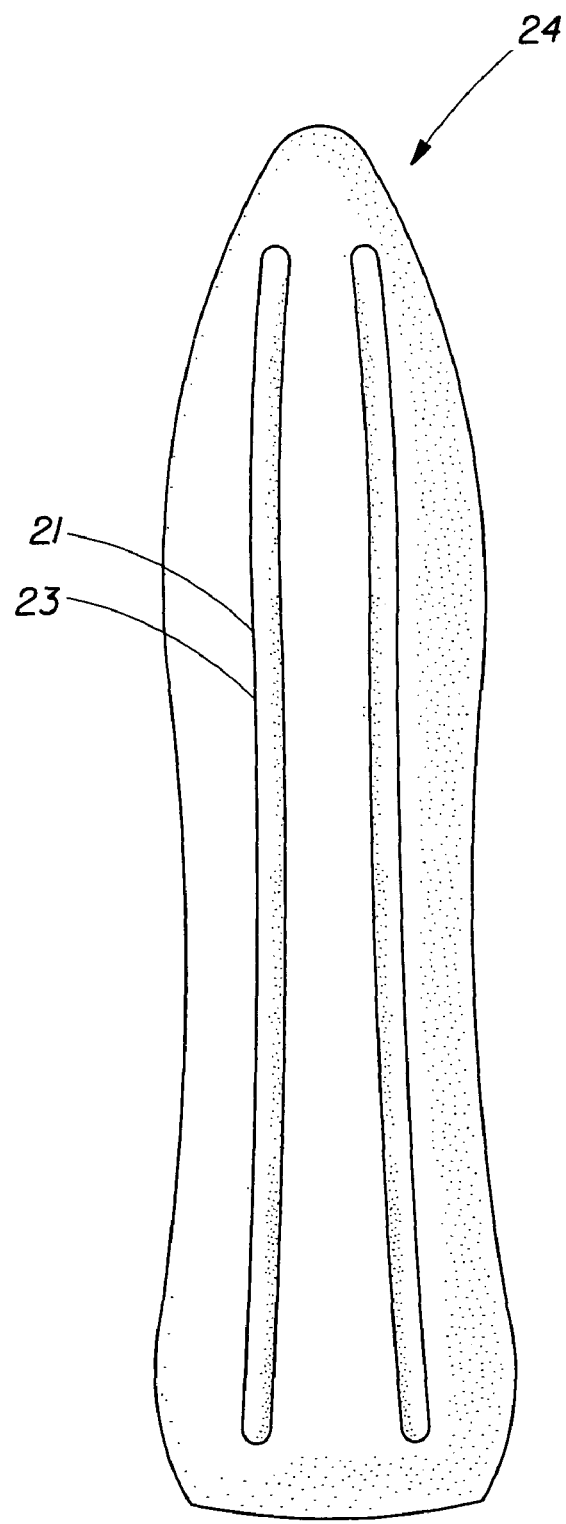
FIG. 5 is a plan view of one embodiment of the tampon of the present invention.
Figure 6:
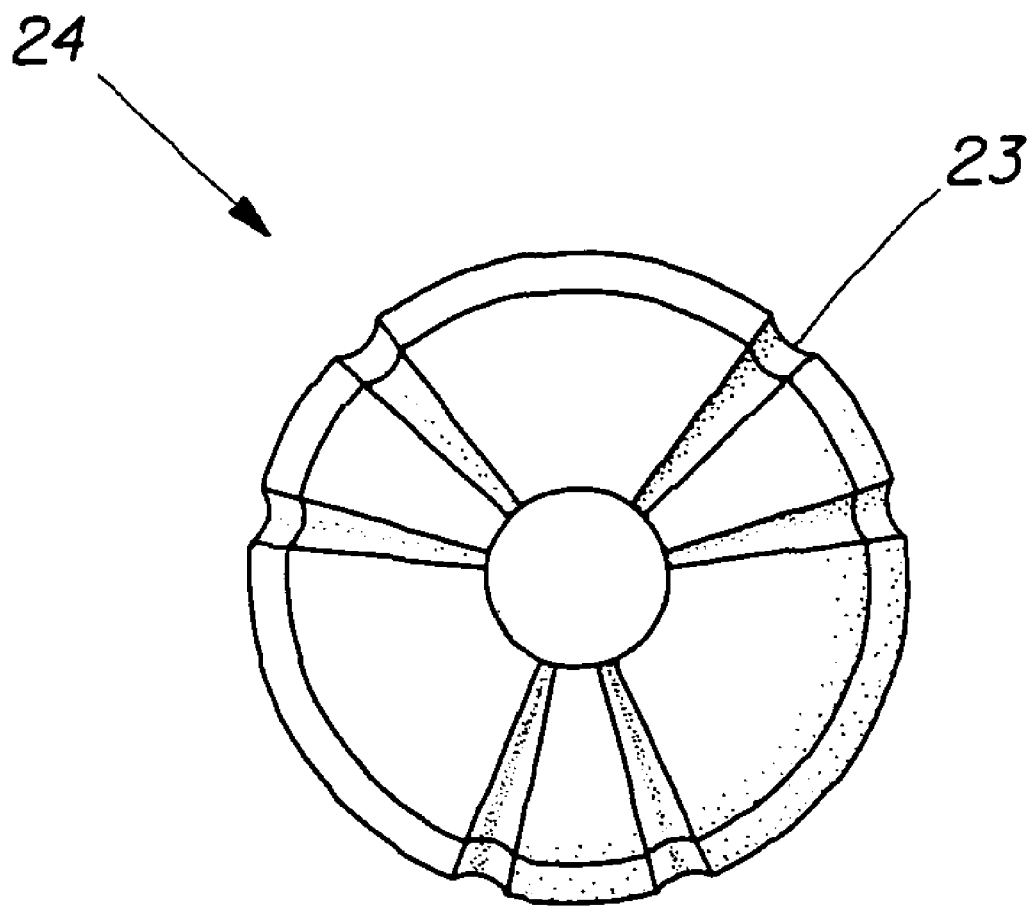
FIG. 6 is a top view of the embodiment in FIG. 5.
Figure 7:
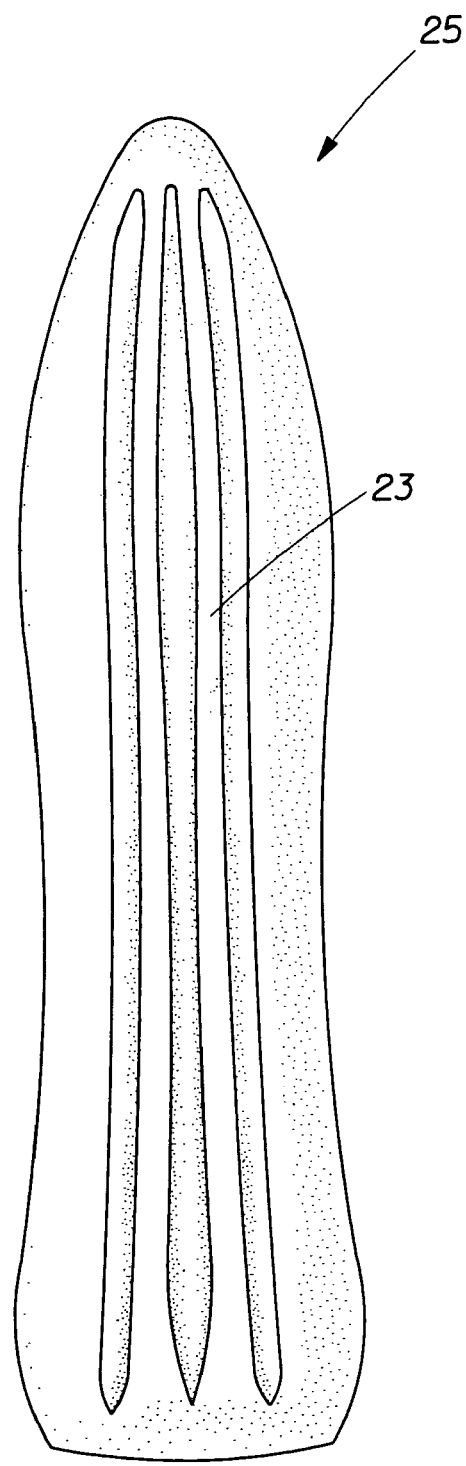
FIG. 7 is a plan view of one embodiment of the tampon of the present invention.
Figure 8:
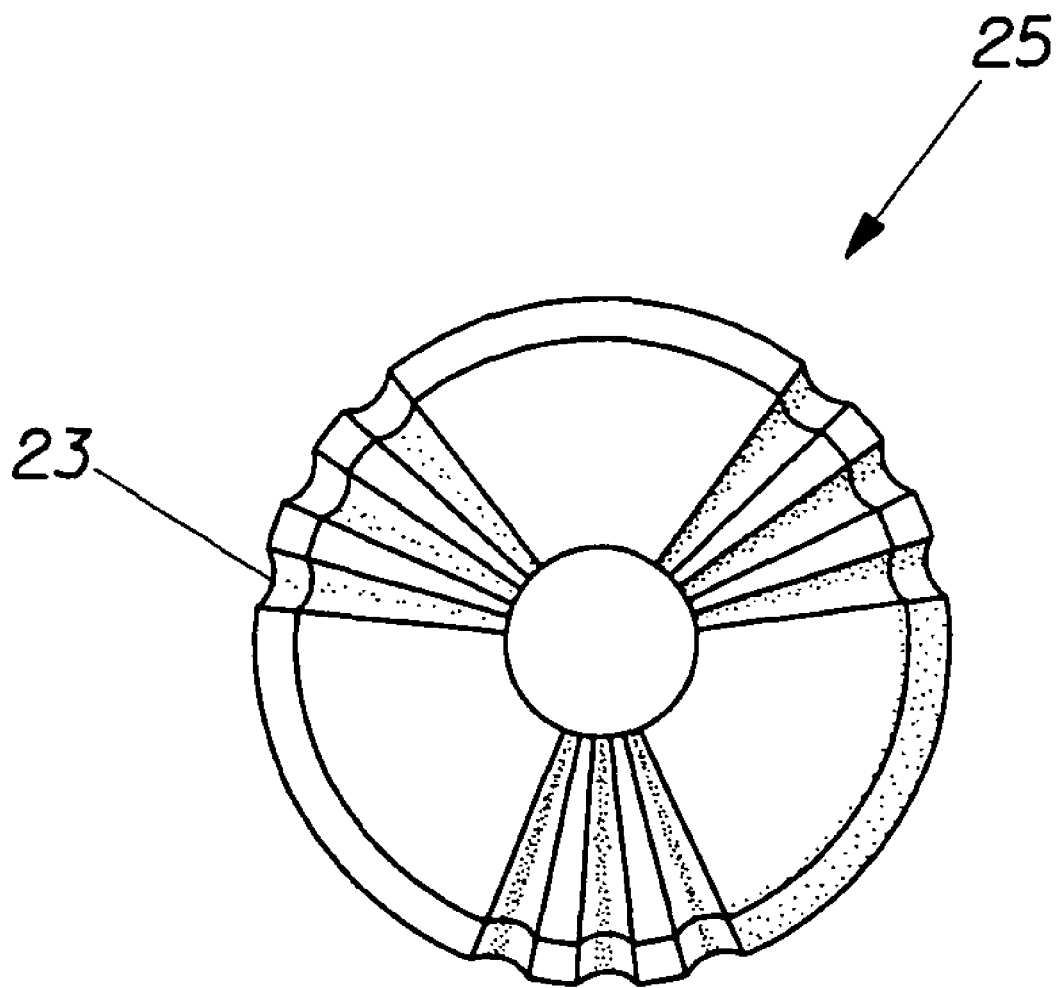
FIG. 8 is a top view of the embodiment in FIG. 7.
Figure 9:
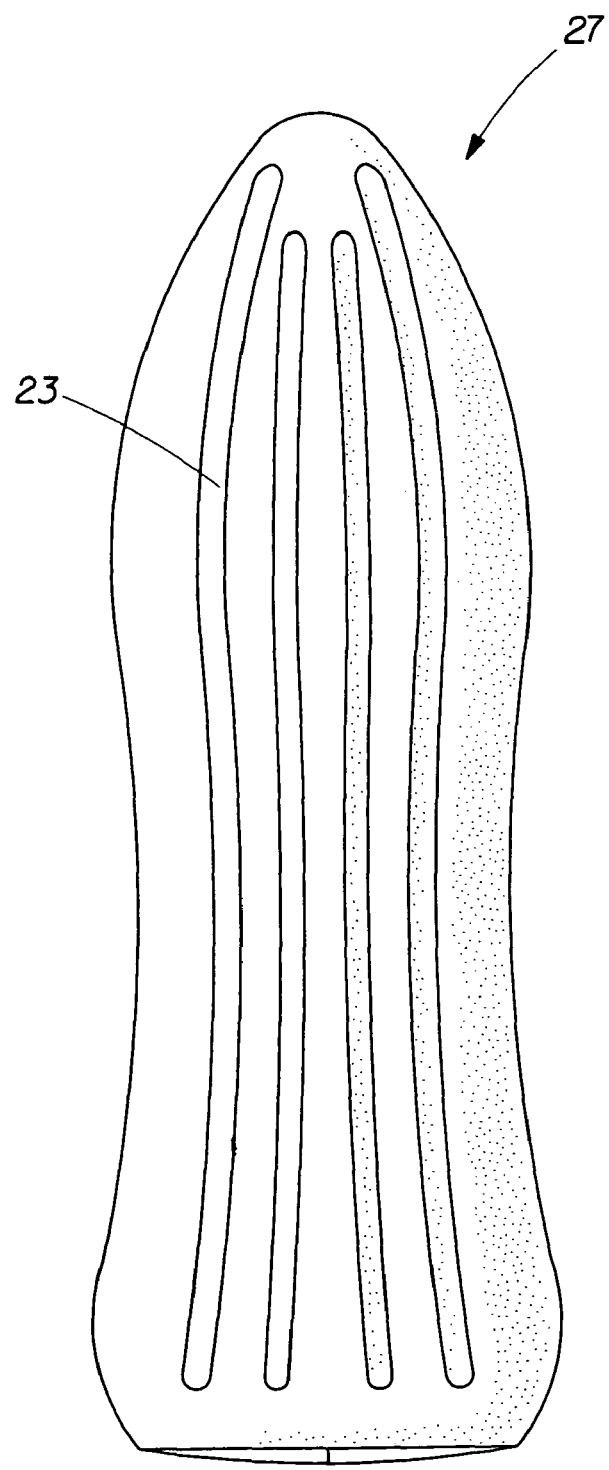
FIG. 9 is a plan view of one embodiment of the tampon of the present invention.
Figure 10:
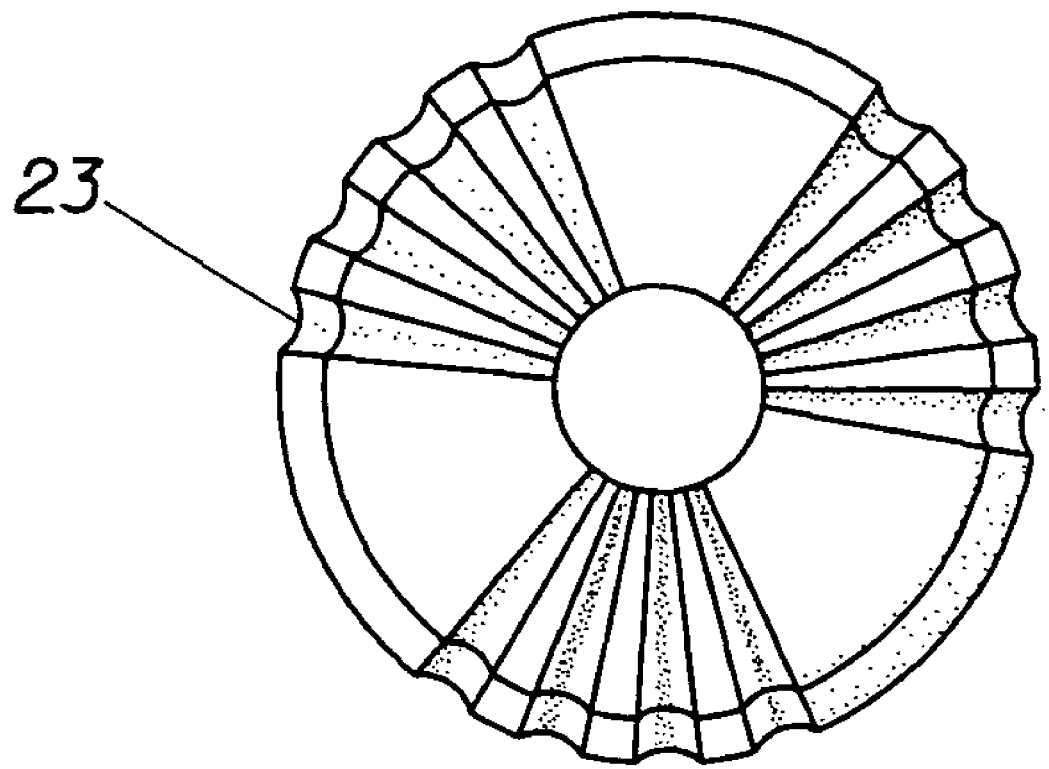
FIG. 10 is a top view of the embodiment in FIG. 9.

Referring to FIGS. 5-10, the line-up consists of an array of tampons comprising light, regular, and extra absorbency tampons enclosed in their respective transparent tampon applicators 50 (not shown). Grooves 23 are indicators. In general, the greater the absorbency of the tampon, the indicator covers a greater surface area of the tampon. FIG. 5 shows a regular absorbency tampon 24 which retains 6-9 grams. Tampon 24 has three sets of two grooves 23. FIG. 6 shows the top view of the tampon 24. Six grooves 23 are shown. FIG. 7 shows a super absorbency tampon 25 which retains 9-12 grams. Tampon 25 has three sets of three grooves 23. FIG. 8 shows the top view of tampon 25. Nine grooves 23 are shown. FIG. 9 shows a superplus absorbency tampon 27. Tampon 27 has three sets of four grooves 23. FIG. 10 shows the top view of tampon 27. Twelve grooves 23 are shown. Thus, this line-up of regular, super, and super-plus tampons enclosed in the tampon applicator 50 (not shown) consist of one indicator which varies in surface area to denote the respective absorbencies of the products within the kits.

Example II

The line-up consists of an array of tampons having grooves as indicators comprising light, regular, and extra absorbency tampons enclosed in substantially transparent tampon applicators 50. A regular absorbency tampon 24 which retains 6-9 grams has grooves covering 20% of the surface area. A super absorbency tampon 25 which retains 9-12 grams has grooves covering 40% of the surface area. A superplus absorbency tampon 27 which retains 12-15 grams has grooves covering 50% of the surface area.

Example III

A "multi-pack" kit comprising light, regular, and extra absorbency tampons enclosed in transparent tampon applicators 50 can be prepared. The kit may consist of three tampons having varying surface areas to denote the respective absorbencies of the products within the kits. The indicator is in the shape of a "T". The "T" is printed on the overwrap of the tampon. The light tampon has 30% of the surface area of the tampon covered by "Ts." The regular tampon has 60% of the surface area of the tampon covered by "Ts." The extra absorbency tampon has 90% of the surface area of the tampon covered by "Ts."

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An array of disposable absorbent articles, said array comprising:
  a.) a first absorbent article being enclosed in a first tampon applicator comprising
    i. an outer surface wherein said outer surface comprises an outer surface area and
    ii. a first indicator comprising a first surface area, wherein said first indicator is disposed on said first absorbent article and corresponds to a first absorbency; and
  b.) a second absorbent article being enclosed in a second tampon applicator comprising
    i. an outer surface wherein said outer surface comprises an outer surface area and
    ii. a second indicator comprising a second surface area, wherein said second indicator is disposed on said second absorbent article and corresponds to a second absorbency;
  c.) wherein said first surface area of said first absorbent article being different than said second surface area of said second absorbent article;
  d.) wherein said first indicator and said second indicator comprise a protuberance or depression.

2. The array of claim 1 wherein said first tampon applicator is transparent, said first tampon applicator reveals said first indicator disposed on said first absorbent article.

3. The array of claim 1 wherein said second tampon applicator is transparent, said second tampon applicator reveals said second indicator disposed on said second absorbent article.

4. The array of claim 1 wherein said first tampon applicator is transparent, said first tampon applicator reveals said first indicator disposed on said first absorbent article and wherein said second tampon applicator is transparent, said second tampon applicator reveals said second indicator disposed on said second absorbent article.

5. The array of claim 1 wherein said second surface area is greater than said first surface area.

6. The array of claim 1 wherein said second absorbency is greater than said first absorbency.

7. The array of claim 1 wherein said outer surface area of said second absorbent article is the same as said outer surface area of said first absorbent article.

8. The array of claim 1 wherein said first indicator is a shape and said second indicator is a shape.

9. The array of claim 8 wherein said shape of said first indicator is the same shape as said shape of said second indicator.

10. The array of claim 8 wherein said shape of said first indicator is a different shape than said shape of said second indicator.

11. The array of claim 1 wherein the protuberance or depression are arranged in a pattern.

12. The array of claim 11 wherein said pattern is selected form the group consisting of spiral lines, diagonal lines, straight lines, checkerboard and mixtures thereof.

13. The array of claim 1 wherein at least one of said first absorbent article or said second absorbent article is selected from the group consisting of tampons, sanitary napkins, sanitary panties, interlabial devices, intravaginal devices, adult incontinence products, diapers, and pantiliners.

14. The tampon according to claim 13 wherein said tampon comprises fibrous material wherein said tampon has varying density over a cross-section of the tampon.

15. An array of disposable absorbent articles, said array comprising:
   a.) a first absorbent article being enclosed in a first tampon applicator comprising
      i. an outer surface wherein said outer surface comprises an outer surface area and
      ii. a first indicator comprising a first surface area, wherein said first indicator is disposed on said first absorbent article and corresponds to a first absorbency; and
   b.) a second absorbent article being enclosed in a second tampon applicator comprising
      i. an outer surface wherein said outer surface comprises an outer surface area and
      ii. a second indicator comprising a second surface area, wherein said second indicator is disposed on said second absorbent article and corresponds to a second absorbency;
   c.) wherein said first surface area of said first absorbent article being the same as said second surface area of said second absorbent article;
   d.) wherein said first indicator and said second indicator comprise a protuberance or depression.

16. The array of claim 15 wherein at least one of said first absorbent article or said second absorbent article is selected from the group consisting of tampons, sanitary napkins, sanitary panties, interlabial devices, intravaginal devices, adult incontinence products, diapers, and pantiliners.

17. An array of disposable absorbent articles, said array comprising:
   a.) a first absorbent article being enclosed in a first tampon applicator comprising
      i. an outer surface wherein said outer surface comprises an outer surface area and
      ii. a first indicator comprising a first surface area, wherein said first indicator is disposed on said first absorbent article and corresponds to a first absorbency; and
   b.) a second absorbent article being enclosed in a second tampon applicator comprising
      i. an outer surface wherein said outer surface comprises an outer surface area and
      ii. a second indicator comprising a second surface area, wherein said second indicator is disposed on said second absorbent article and corresponds to a second absorbency;
   c.) wherein said first surface area of said first absorbent article being the same as said second surface area of said second absorbent article;
   d.) wherein said first indicator and said second indicator comprise a protuberance or depression.

18. The array of claim 17 wherein said first tampon applicator and said second tampon applicator are transparent.

\* \* \* \* \*